(12) United States Patent
Dev et al.

(10) Patent No.: US 7,795,306 B2
(45) Date of Patent: *Sep. 14, 2010

(54) TRITERPENE DERIVATIVES FOR THE TREATMENT OF CANCER AND INFLAMMATORY DISEASE BY INHIBITION OF NF-κB

(76) Inventors: Inderjit Kumar Dev, 4211 Cobscook Dr., Durham, NC (US) 27707; Ven Subbiah, 142 Brochion Ridge Dr., Garner, NC (US) 27529

( * ) Notice: Subject to any disclaimer, the term of this patent is extended or adjusted under 35 U.S.C. 154(b) by 0 days.

This patent is subject to a terminal disclaimer.

(21) Appl. No.: 12/280,748

(22) PCT Filed: Mar. 1, 2007

(86) PCT No.: PCT/US2007/063070

§ 371 (c)(1),
(2), (4) Date: Aug. 26, 2008

(87) PCT Pub. No.: WO2007/103727

PCT Pub. Date: Sep. 13, 2007

(65) Prior Publication Data

US 2009/0036524 A1     Feb. 5, 2009

Related U.S. Application Data

(60) Provisional application No. 60/779,141, filed on Mar. 3, 2006.

(51) Int. Cl.
*A61K 31/21* (2006.01)
(52) U.S. Cl. .................................................. 514/510
(58) Field of Classification Search .................. 514/510
See application file for complete search history.

(56) References Cited

U.S. PATENT DOCUMENTS

| | | | |
|---|---|---|---|
| 5,220,930 | A | 6/1993 | Gentry |
| 5,248,807 | A | 9/1993 | Fujimoto et al. |
| 5,320,131 | A | 6/1994 | Dull |
| 5,463,107 | A | 10/1995 | Konoike et al. |
| 5,587,505 | A | 12/1996 | Konoike et al. |
| 5,944,026 | A | 8/1999 | Kopsch et al. |
| 6,615,843 | B2 | 9/2003 | Pera |
| 6,766,803 | B2 | 7/2004 | An |
| 2005/0165087 | A1 | 7/2005 | Callahan et al. |

OTHER PUBLICATIONS

Bremner, Paul and Michael Heinrich, Natural Products as Targeted Modulators of the Nuclear Factor-kB Pathway, Journal of Pharmacy and Pharmacology, 2002, 54: 453-472, JPP, London UK.
McNulty, Susan E., Raul Del Rosario, Dazhi Cen, Frank L. Meyskens Jr. and Sun Yang, Comparative Expression of Normal Skin vs. Benign Intradermal Naevus and Human Metastatic Melanoma Biopsies, Pigment Cell Research, Apr. 2004, p. 173, vol. 17 Issue 2.
Sakurawi, Kensuke, Fumio Yasuda, Takehiko Tozyo, Miharu Nakamura, Tomohiro Sato, Junko Kikuchi, Yoshihiro Terui, Yuji Ikenishi, Tsuyoshi Iwata, Kazuhiro Takahashi, Toshiro Konoike, Shin-Ichi Mihara, and Masafumi Fujimoto, Endothelin Receptor Antagonist Triterpenoid, Myriceric Acid A, Isolated from *Myrica cerifera*, and Structure Activity Relationship of Its Derivatives, Chem. Pharm. Bull., Feb. 1996, 44(2) 343-351, Pharmaceutical Society of Japan.
Mihara, Shin-Ichi, Fumiyo Tozawa, Kohji Itazaki, and Masafumi Fujimoto, Binding Characterization of [3H]S-0139, and Antagonist of the Endothelin ETA Receptor Subtype, European Journal of Pharmacology, 1998, 342 (1998) 319-324, Elsevier Science B.V.
Benigni, Ariela, Norberto Perico, and Giuseppe Remuzzi, The Potential of Endothelin Antagonism as a Therapeutic Approach, Monthly Focus: Cardiovascular & Renal, 2004, 13(11):1419-1435, Ashley Publications Ltd.
Mihara, Shin-Ichi, Shigeyuki Nakajima, Shoichi Matumura, Toshiro Kohnokike, and Masafumi Fujimoto, Pharmacological Characterization of a Potent Nonpeptide Endothelin Receptor Antagonist, 97-139, The Journal of Pharmacology and Experimental Therapeutics, 1994, 1122-1128, vol. 268, No. 3, The American Society for Pharmacology and Experimental Therapeutics, USA.
McKay, Lorraine I. and John A. Cidlowski, Molecular Control of Immune/Inflammatory Responses: Interactions Between Nuclear Factor-kB and Steroid Receptor-Signaling Pathways, Endocrine Reviews, 1999, 20(4): 435-459, The Endocrine Society.
Dinkova-Kostova, Albena T., Karen T. Liby, Katherine K. Stephenson, W. David Holtzclaw, Ziangqun Gao, Nanjoo Suh, Charlotte Williams, Renee Risingsong, Tadashi Honda, Gordon W. Gribble, Michael B. Sporn, and Paul Talalay, Extremely Potent Triterpenoid Inducers of the Phase 2 Response: Correlations of Protection Against Oxidant and Inflammatory Stress, Medical Sciences, Mar. 22, 2005, 4584-4589, vol. 102, No. 12, The National Academy of Sciences of the USA.

*Primary Examiner*—Kamal A Saeed
*Assistant Examiner*—Samantha L Shterengarts
(74) *Attorney, Agent, or Firm*—Jim Passé; Passé Intellectual Property, LLC

(57) ABSTRACT

The present invention relates to the use of triterpenes of the formula (I): which are inhibitors of nuclear factor kappa B (NF-κB for use in the treatment of inflammatory diseases and for cancers susceptible to an NF-κB inhibitor. The present invention also relates to compounds and methods useful to inhibit cell proliferation and for the induction of apoptosis.

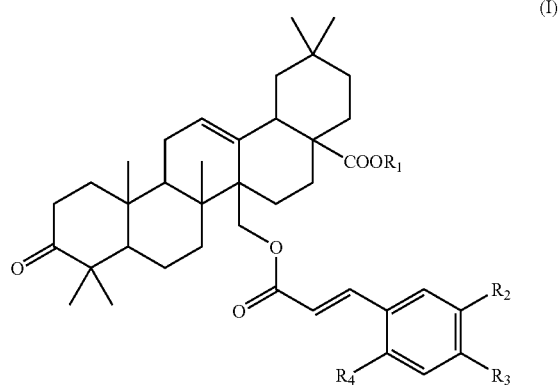

(I)

3 Claims, 1 Drawing Sheet

TRITERPENE DERIVATIVES FOR THE TREATMENT OF CANCER AND INFLAMMATORY DISEASE BY INHIBITION OF NF-κB

This application claims priority of U.S. Application Ser. No. 60/779,141 filed on Mar. 3, 2006 and incorporated herein in its entirety by reference.

BACKGROUND OF THE INVENTION

1. Field of the Invention

This invention relates to the use of certain triterpenes which are inhibitors of nuclear factor kappa B (NF-$_κ$B). In particular, it relates to useful triterpenes and pharmaceutical compositions containing them for use in the treatment of inflammatory diseases and for cancers susceptible to an NF-$_κ$B inhibitor. The present invention also relates to compounds and methods useful to inhibit cell proliferation and for the induction of apoptosis.

2. Description of the Related Art

Certain triterpenes have previously been known to inhibit the activity of the endothelin receptor by acting as a receptor antagonist. In U.S. Pat. No. 5,587,505 to Konoike issued Dec. 24, 1996, U.S. Pat. No. 5,463,107 to Konoike issued Oct. 31, 1995 and U.S. Pat. No. 5,248,807 to Fujimoto issued Sep. 28, 1993 there are described certain triterpenes active as an antagonist against the endothelin receptor. These compounds are described as useful in treatment of disease states that are caused by excessive secretion of endothelin. These compounds are further shown to be a competitor of endothelin for binding to the endothelin receptor. No further activity or use is described.

Endothelin is a vasoconstrictor peptide composed of 21 amino acids and derived in mammals from the endothelium. These endothelin receptors exist in various tissue and organs such as vessels, trachea and the like and their excessive stimulation can lead to circulatory diseases such as pulmonary hypertension, acute and chronic heart failure, acute and chronic renal failure, atherosclerosis, cerebrovascular diseases and the like.

NF-$_κ$B is one of the principal inducible transcription factors in mammals and has been shown to play a pivotal role in the mammalian innate immune response and chronic inflammatory conditions (Jour. Pharm. and Phar. 2002, 54: 453-472). The signaling mechanism of NF-$_κ$B involves an integrated sequence of protein-regulated steps and many are potential key targets for intervention in treating certain NF-$_κ$B cascade dependant inflammatory conditions and cancers.

More specifically, the family of NF-$_κ$B transcription factors comprises important regulatory proteins that impact virtually every feature of cellular adaptation, including responses to stress, inflammatory reactions, activation of immune cell function, cellular proliferation, programmed cell death (apoptosis), differentiation and oncogenesis (1). NF-$_κ$B regulates more than 150 genes, including cytokines, chemokines, cell adhesion molecules, and growth factors (2). It is therefore not surprising that diseases result when NF-$_κ$B-dependent transcription is not appropriately-regulated. NF-$_κ$B has been implicated in several pathologies, including certain cancers (e.g., Hodgkin's disease, breast cancer, and prostate cancer), diseases associated with inflammation (e.g., rheumatoid arthritis, asthma, inflammatory bowel disease (e.g., Crohn's disease and ulcerative colitis), alcoholic liver disease, non-alcoholic steatohepatitis, pancreatitis, primary dysmenorrhea, psoriasis, and atherosclerosis) and Alzheimer's disease. Several mediators of inflammation are under the influence of activated NF-$_κ$B including inducible nitric oxide synthase, the subsequent production of nitric oxide and prostaglandin synthase. It has further been shown that compounds which interfere with COX-2 act via the inhibition of NF-$_κ$B. NF-$_κ$B consists of different combinations of Rel proteins in various heterodimers and homodimers and has previously been represented by the subunits p65/p50. All the Rel proteins share a conserved region of 300 amino acids at the N-terminal responsible for DNA-binding, dimerisation and interaction with the NF-$_κ$B inhibitory protein I-kappaB. NF-$_κ$B is responsible in several signaling cascades and the two most important of which are ones associated with mammalian immune response of the interleukin/lipopolysaccharide pathway. There are pathways involved with NF-$_κ$B that are critically involved in apoptosis. NF-$_κ$B binding by RelA is constituitively elevated in human metastatic melanoma cultures relative to normal melanocytes.

NF-$_κ$B is a collective name for dimeric transcription factors comprising the Rel family of DNA-binding proteins (3, 4). All members of this family are characterized by the presence of a conserved protein motif called the Rel homology domain (RHD) that is responsible for dimer formation, nuclear translocation, sequence-specific DNA recognition and interaction with inhibitory proteins collectively known as I-$_κ$B. Any homodimer or heterodimer combination of family members constitutes NF-$_κ$B.

Regulation of NF-$_κ$B Activity

The activity of NF-$_κ$B is regulated through an assortment of complex signaling pathways. NF-$_κ$B is negatively regulated through interaction with I-$_κ$B (5). Each I-$_κ$B possesses an N-terminal regulatory domain for a signal dependent I-$_κ$B proteolysis, a domain composed of six or seven ankyrin repeats to mediate interaction with the RelI proteins, and a C-terminal domain containing a PEST motif that is implicated in constitutive I-$_κ$B turnover. Inactive forms of NF-$_κ$B reside in the cytoplasm as NF-$_κ$B/I-$_κ$B complexes, because I-$_κ$B binding to NF-$_κ$B blocks the ability of the nuclear import proteins to recognize and bind to the nuclear localization signal in the RHD.

NF-$_κ$B activation occurs when NF-$_κ$B is translocated to the nucleus following its release from I-$_κ$B. I-$_κ$B dissociation arises through its phosphorylation by an inducible I-$_κ$B kinase (IKK) and ubiquitination by I-$_κ$B ubiquitin ligase, which flags it for proteolysis by the 26S proteosome. Since the ubiquitin ligase and the 26S proteosome are constitutively expressed, the de-repression of NF-$_κ$B functional activity is largely governed by those signals that induce the expression of IKK, which include inflammatory cytokines, mitogens, viral proteins, and stress.

IKK is also known as the signalsome, which consists of a large multi-subunit complex containing the catalytic subunits IKK.alpha./IKK-1 and IKK.beta./IKK-2, a structural subunit termed NF-$_κ$B essential modulator (NEMO), as well as perhaps other components (6, 7). NEMO, also known as IKK.γ. and IKKAP-1, functions as an adapter protein to permit communication between the catalytic subunits and upstream activators (7). Activation of NF-$_κ$B is a tightly controlled process and cannot occur without NEMO (8, 9).

Protein phosphorylation positively regulates NF-$_κ$B activity (1). Protein phosphorylation enhances the transcriptional activity of NF-$_κ$B, presumably through the phosphorylated protein's interaction with other transcriptional co-activators. Protein kinase A (PKA), casein kinase II (CKII), and p38 mitogen-activated protein kinase (MAPK) have been implicated in the phosphorylation of NF-$_κ$B.

The activity of NF-$_κ$B is also subject to autoregulatory mechanisms to ensure that NF-$_κ$B-dependent transcription is coordinately-linked to the signal-inducing response. For example, the I-$_κ$B genes contain NF-$_κ$B binding sites within their promoter structures that result in their increased transcription upon NF-$_κ$B binding. The expressed I-$_κ$B proteins migrate into the nucleus to bind the NF-$_κ$B and mediate transport of NF-$_κ$B to the cytoplasm where it remains inactive.

Role of NF-κB in Disease and Disorders

NF-κB contributes to progression of cancers by serving both as positive regulators of cell growth and as a negative regulator of apoptosis (10, 11). NF-κB stimulates expression of cell cycle-specific proteins c-Myc and cyclin D1 (12, 13). The constitutive expression of these proteins results in sustained cell proliferation. Continued expression of c-Myc ultimately leads to apoptosis. NF-κB can block c-Myc's apoptosis effects, thereby stimulating proliferation without cytotoxicity. NF-κB also inhibits the ability of Tumor Necrosis Factor (TNF) to induce cell death as well as protect cells from the effects of ionizing radiation and chemotherapeutic drugs (14). Thus, NF-κB promotes both hyperplasia and resistance to oncological treatments, which are hallmarks of many cancers.

Inhibition of NF-κB activation has been linked to the chemopreventive properties of several anti-cancer compounds (e.g., selenium, flavonoids, etc.) (15, 16). Although long-term inhibition could have unwanted effects on immune response, down-regulation of NF-κB activity is considered a very attractive strategy for developing new cancer treatments.

Recently, Shen et al. demonstrated that certain oligonucleotides that contain polyguanonsines are potent inhibitors of the proliferation of murine prostate cancer cells (17). The specific DNA-binding activities of NF-κB and another transcription factor, AP-1 were reduced in cells treated with these oligonucleotides. Oligonucleotides displaying antiproliferative effects were capable of forming higher order structures containing guanosine-quartets (G-quartets). The requirement of G-quartets for inducing apoptosis was suggested by experimental observations wherein mutations that destroyed the capacity to form a G-quartet structure correlated with abolishment of the antitumor activities of the oligonucleotide (17).

In the case of inflammation, NF-κB plays important roles in both the initiation and maintenance of the inflammatory response (1). Activated T cells, such as activated $CD_4+$ T helper cells, trigger immune inflammation. The T helper cell population can differentiate further to two subset populations that have opposite effects on the inflammatory response. The Th1 subset is considered proinflammatory, as these cells mediate cellular immunity and activate macrophages. The Th2 subset is considered anti-inflammatory, as these cells mediate humoral immunity and down-regulate macrophage activation. The subsets are distinguishable by the different types of cytokine profiles that they express upon differentiation. NF-κB stimulates production of cytokine profiles characteristic of the Th1 subset type, leading to a proinflammatory response. Conversely, suppression of NF-κB activation leads to production of cytokine profiles characteristic of the Th2 subset type that mediates an anti-inflammatory response.

Once activated, these inflammatory cytokines and growth factors can act through autocrine loops to maintain NF-κB activation in non-immune cells within the lesion (1). For example, NF-κB regulates the expression of cytokines Interleukin 1 β (IL-1 β) and Tumor Necrosis Factor alpha (TNFα), which are considered essential mediators of the inflammatory response. Conversely, these gene products positively activate NF-κB expression that leads to persistence of the inflammatory state. For example, TNF products have been implicated in promoting inflammation in several gastrointestinal clinical disorders that include: alcoholic liver disease, non-alcoholic steatohepatitis, prancreatitis (including chronic, acute and alcohol-induced), and inflammatory bowel disorders, such as ulcerative colitis and Crohn's Disease.

Continued NF-κB activation also promotes tissue remodeling in the inflammatory lesions (1). Several NF-κB-responsive genes have been implicated in this regard and include growth factors that are important to neovascularization (e.g., VEGF), matrix proteinases (including metalloproteases), cyclooxygenase, nitric oxide synthase, and enzymes that are involved in the synthesis of proinflammatory prostaglandins, nitric oxide, and nitric oxide metabolites (1). Such tissue remodeling is often accompanied by breakdown of healthy cells as well as by hyperplasia, both of which are often observed in rheumatoid arthritis and other inflammatory diseases (1).

Suppression of NF-κB activity alleviates many inflammatory disease conditions and increases the susceptibility of certain cancers to effective treatment. Several anti-inflammatory drugs directly target the NF-κB signaling pathway. Glucocorticoids, one member of the general steroid family of anti-inflammatory drugs, interfere with NF-κB function through the interaction of the glucocorticoid receptor with NF-κB (18). Gold compounds interfere with the DNA-binding activity of NF-κB (19). Aspirin and sodium salicylate, as representatives of non-steroid anti-inflammatory drugs, inhibit IKKβ activity and thereby prevent signal-inducible I-κB turnover (20). Dietary supplements with anti-inflammatory and anti-tumor activities prevent NF-κB activation by interfering with pathways leading to IKK activation. Vitamins C and E, prostaglandins, and other antioxidants, scavenge reactive oxygen species that are required for NF-κB activation (21, 22). Specific NF-κB decoys that mimic natural NF-κB ligands (e.g., synthetic double-stranded oligodeoxynucleotides that contain the NF-κB binding site) can suppress NF-κB activity and prevent recurrent arthritis in animal models (23).

Despite the promise of anti-inflammatory drugs in treating inflammatory diseases, many diseases are non-responsive to these modalities. For example, many patients with chronic inflammatory diseases, such as Crohn's disease, fail to respond to steroid treatment. Recent studies suggest that one basis for the steroid unresponsiveness may be attributed to NF-κB and other NF-κB-responsive gene products antagonizing glucocorticoid receptor expression, which is necessary for the steroid's anti-inflammatory activity (24).

Alzheimer's disease represents another example of a condition that displays an inflammatory component in its pathogenesis. Recent studies indicate that abnormal regulation of the NF-κB pathway may be central to the pathogenesis of Alzheimer's disease. NF-κB activation correlates with the initiation of neuritic plaques and neuronal apoptosis during the early phases of the disease. For example, NF-κB immunoreactivity is found predominantly in and around early neuritic plaque types, whereas mature plaque types display reduced NF-κB activity (25).

Numerous plant-derived products have been identified as inhibitors of NF-κB activation and a large number of pure compounds have been shown to interfere with the cascade leading to NF-κB activation. While these compositions are clearly useful to date and many agents which inhibit NF-κB also inhibit AP-1 in certain U937 cells, no compositions which also inhibit endothelin have been discovered.

Accordingly it would be extremely useful to find compositions which can inhibit both endothelin and NF-κB.

SUMMARY OF THE INVENTION

It has been discovered that certain compositions represented by formula I which previously have only been known to inhibit endothelin also inhibit NF-κB and are thus useful to treat certain conditions not previously known to be susceptible to treatment with an endothelin antagonist alone.

In one embodiment of the invention there is disclosed a method of preventing or treating cancer or an inflammatory disease in a mammal in need of such treatment comprising administering a NF-κB inhibitory effective amount of a composition of the formula:

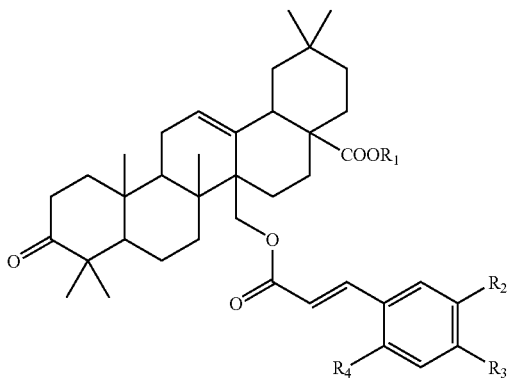

wherein $R_1$ is hydrogen or a metabolic ester residue; $R_2$ and $R_3$ each independently or together are hydrogen or hydroxy; $R_4$ is hydrogen or $NHR_5$; wherein $R_5$ is $R_6$—$R_7$; wherein $R_6$ is —SO—, —COCOO—, or —$COR_8COO$— ($R_8$ is an alkyl chain of 1 to 6 carbon atoms or an alkene-bearing chain of 2 to 6 carbon atoms) and $R_7$ is hydrogen or a metabolic ester residue or a pharmaceutically acceptable salt thereof.

In another embodiment of the invention there is a method inducing apoptosis in a selected mammalian cell comprising administering to the cell an effective amount of a compound of the formula:

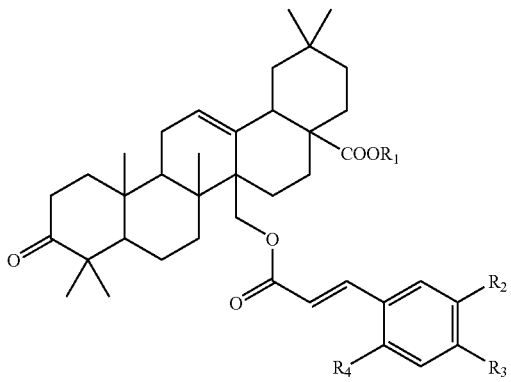

wherein $R_1$ is hydrogen or a metabolic ester residue; $R_2$ and $R_3$ each independently or together are hydrogen or hydroxy; $R_4$ is hydrogen or $NHR_5$; wherein $R_5$ is $R_6$—$R_7$; wherein $R_6$ is —SO3-, —COCOO—, or —$COR_8COO$— ($R_8$ is an alkyl chain of 1 to 6 carbon atoms or an alkene-bearing chain of 2 to 6 carbon atoms) and $R_7$ is hydrogen or a metabolic ester residue or a pharmaceutically acceptable salt thereof.

Other embodiments of the invention will be clear from the discovery that the compounds of the invention posses NF-$_\kappa$B inhibitory activity and are therefore useful for the treatment of disease other than possible with just endothelin antagonist activity previously known. It is an object of the invention to treat mammals with compositions of the invention used as inhibitors of NF-$_\kappa$B with anti-inflammatory, anti-proliferative, immuno-suppressive, cytoprotective and antiviral activity.

DETAILED DESCRIPTION OF THE INVENTION

Figure 1:
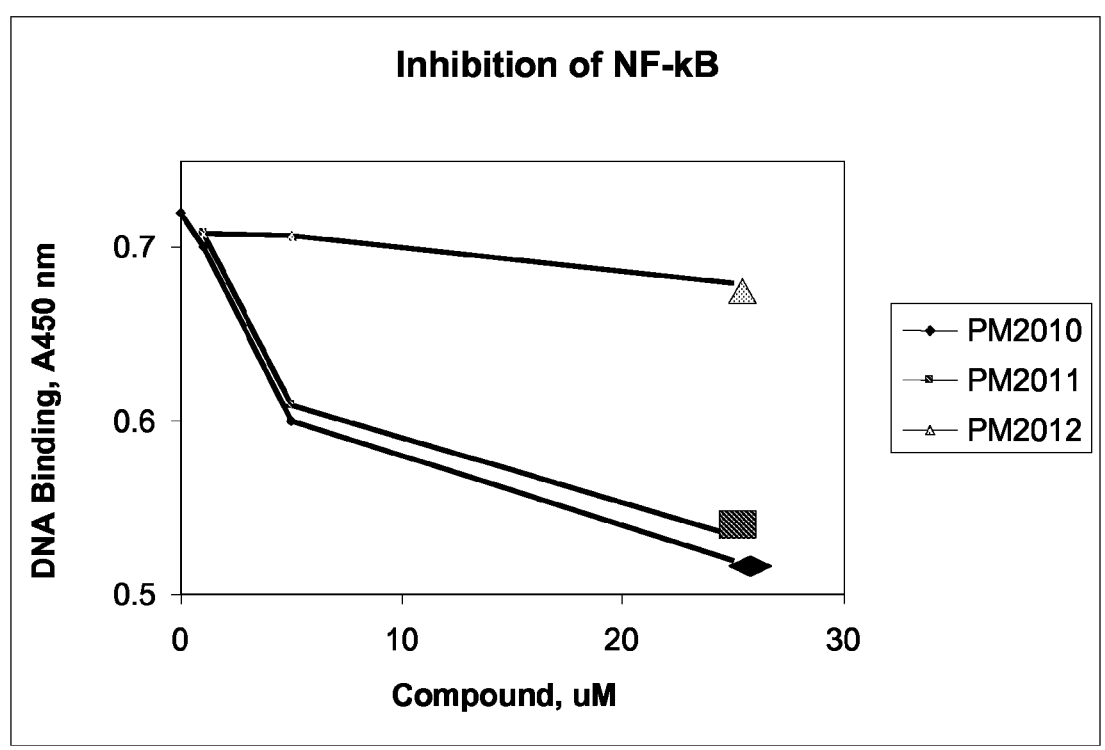
FIG. 1 shows the dose-dependent inhibition of NF-$_\kappa$B activation by a composition of formula I (also called PM2011).

The methods of the invention relate to compositions useful for inhibiting NF-$_\kappa$B of formula I:

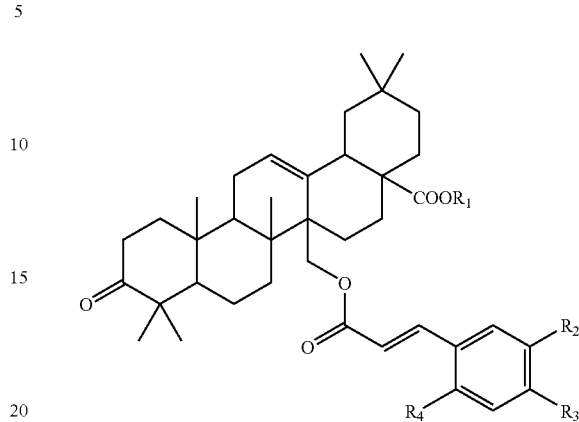

wherein $R_1$ is hydrogen or a metabolic ester residue; $R_2$ and $R_3$ each independently or together are hydrogen or hydroxy; $R_4$ is hydrogen or $NHR_5$; wherein $R_5$ is $R_6$—$R_7$; wherein $R_6$ is —SO3-, —COCOO—, or —$COR_8COO$— ($R_8$ is an alkyl chain of 1 to 6 carbon atoms or an alkene-bearing chain of 2 to 6 carbon atoms) and $R_7$ is hydrogen or a metabolic ester residue or a pharmaceutically acceptable salt thereof.

This invention provides methods for treating a variety of diseases associated with NF-$_\kappa$B activation including cancer and inflammatory and tissue repair disorders; particularly rheumatoid arthritis, inflammatory bowel disease, asthma and COPD (chronic obstructive pulmonary disease) osteoarthritis, osteoporosis and fibrotic diseases; dermatosis, including psoriasis, atopic dermatitis and ultraviolet radiation (UV)-induced skin damage; autoimmune diseases including systemic lupus eythematosus, multiple sclerosis, psoriatic arthritis, alkylosing spondylitis, tissue and organ rejection, Alzheimer's disease, stroke, atherosclerosis, restenosis, diabetes, glomerulonephritis, cancer, including Hodgkins disease, cachexia, inflammation associated with infection and certain viral infections, including acquired immune deficiency syndrome (AIDS), adult respiratory distress syndrome, and Ataxia Telangiestasia.

The present invention includes all hydrates, solvates, complexes and prodrugs of the compounds of this invention. Prodrugs are any covalently bonded compounds, which release the active parent, drug according to Formula I in vivo. If a chiral center or another form of an isomeric center is present in a compound of the present invention, all forms of such isomer or isomers, including enantiomers and diastereomers, are intended to be covered herein. Inventive compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether or not existing in predominantly one form.

The meaning of any substituent at any one occurrence in Formula I or any subformula thereof is independent of its meaning, or any other substituent's meaning, at any other occurrence, unless specified otherwise.

As used herein, "metabolic ester residue" refers to an ester residue which decomposes to reproduce carboxylic acids in a living body. See for example U.S. Pat. No. 5,248,807 which describes metabolic ester residue triterpene derivatives.

This invention provides a pharmaceutical composition, which comprises a compound according to Formula I and a pharmaceutically acceptable carrier, diluent or excipient. Accordingly, the compounds of Formula I may be used in the manufacture of a medicament. Pharmaceutical compositions of the compounds of Formula I prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filing for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

Typical compositions for inhalation are in the form of a dry powder, solution, suspension or emulsion. Administration may for example be by dry powder inhaler (such as unit dose or multi-dose inhaler, or by nebulisation or in the form of a pressurized aerosol. Dry powder compositions typically employ a carrier such as lactose, trehalose or starch. Compositions for nebulisation typically employ water as vehicle. Pressurized aerosols typically employ a propellant such as dichlorodifluoromethane, trichlorofluoromethane or, more preferably, 1,1,1,2-tetrafluoroethane, 1,1,1,2,3,3,3-heptafluoro-n-propane or mixtures thereof. Pressurized aerosol formulations may be in the form of a solution (perhaps employing a solubilising agent such as ethanol) or a suspension which may be excipient free or employ excipients including surfactants and/or co-solvents (e.g. ethanol). In dry powder compositions and suspension aerosol compositions the active ingredient will preferably be of a size suitable for inhalation (typically having mass median diameter (MMD) less than 20 microns, e.g., 1-10 especially 1-5 microns). Size reduction of the active ingredient may be necessary, e.g., by micronisation.

Typical compositions for nasal delivery include those mentioned above for inhalation and further include non-pressurized compositions in the form of a solution or suspension in an inert vehicle such as water optionally in combination with conventional excipients such as buffers, anti-microbials, tonicity modifying agents and viscosity modifying agents which may be administered by nasal pump.

For rectal administration, the compounds of this invention may also be combined with excipients such as cocoa butter, glycerin, gelatin or polyethylene glycols and molded into a suppository.

The methods of the present invention include topical inhaled and intracolonic administration of the compounds of Formula I. By topical administration is meant non-systemic administration, including the application of a compound of the invention externally to the epidermis, to the buccal cavity and instillation of such a compound into the ear, eye and nose, wherein the compound does not significantly enter the blood stream. By systemic administration is meant oral, intravenous, intraperitoneal and intramuscular administration. The amount of a compound of the invention (hereinafter referred to as the active ingredient) required for therapeutic or prophylactic effect upon topical administration will, of course, vary with the compound chosen, the nature and severity of the condition being treated and the animal undergoing treatment, and is ultimately at the discretion of the physician.

While it is possible for an active ingredient to be administered alone as the raw chemical, it is preferable to present it as a pharmaceutical formulation. The active ingredient may comprise, for topical administration, from 0.01 to 5.0 wt % of the formulation.

The topical formulations of the present invention, both for veterinary and for human medical use, comprise an active ingredient together with one or more acceptable carriers therefore and optionally any other therapeutic ingredients. The carrier must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required such as: liniments, lotions, creams, ointments or pastes, and drops suitable for administration to the eye, ear or nose.

Utility of the Present Invention

The compounds of Formula I are useful as inhibitors of NF-$_\kappa$B activation. The present method utilizes compositions and formulations of said compounds, including pharmaceutical compositions and formulations of said compounds. The present invention particularly provides methods of treatment of diseases associated with inappropriate NF-$_\kappa$B activation, which methods comprise administering to an animal, particularly a mammal, most particularly a human in need thereof one or more compounds of Formula I. The present invention particularly provides methods for treating inflammatory and tissue repair disorders, particularly rheumatoid arthritis, inflammatory bowel disease, asthma and COPD (chronic obstructive pulmonary disease); osteoarthritis, osteoporosis and fibrotic diseases; dermatosis, including psoriasis, atopic dermatitis and ultraviolet radiation (UV)-induced skin damage, autoimmune diseases including systemic lupus eythematosus, multiple sclerosis, psoriatic arthritis, alkylosing spondylitis, tissue and organ rejection, Alzheimer's disease, stroke, atherosclerosis, restenosis, diabetes, glomerulonephritis, cancer, including Hodgkins disease, cachexia, inflammation associated with infection and certain viral infections, including aquired immune deficiency syndrome (AIDS), adult respiratory distress syndrome and Ataxia Telangiestasia.

For acute therapy, parenteral administration of one or more compounds of Formula I is useful. An intravenous infusion of the compound in 5% dextrose in water or normal saline, or a similar formulation with suitable excipients, is most effective, although an intramuscular bolus injection is also useful. Typically, the parenteral dose will be about 0.01 to about 50 mg/kg; preferably between 0.1 and 20 mg/kg, in a manner to maintain the concentration of drug in the plasma at a concentration effective to inhibit activation of NF-$_\kappa$B. The compounds are administered one to four times daily at a level to achieve a total daily dose of about 0.4 to about 80 mg/kg/day. The precise amount of a compound used in the present method which is therapeutically effective, and the route by which such compound is best administered, is readily determined by one of ordinary skill in the art by comparing the blood level of the agent to the concentration required to have a therapeutic effect.

EXAMPLES

Example 1

Extraction, Isolation, Purification and Identification of PM 2011 (1)

Extraction and purification of active compounds from clary sage root: Roots were collected from the ten-months-old clary sage (*Salvia sclarea* L.) plants after the aerial parts were harvested for its essential oil and sclareol. The roots were washed in tap water, air dried at 45° C. and ground in a Willey mill (10 u size particles). Three aliquots of 150 g of the powder was extracted with 1 L ethyl acetate in a soxhlet extractor at 26° C. for 2 hr. The crude extract (1.0 gram) was purified via flash column chromatography using silica gel.

Silica gel column chromatography: Medium pressure flash column chromatography was carried out using silica gel 60 (230-400 mesh). A glass column with a 30 mm diameter and 1000 mm length was packed with silica gel in hexane slurry. The crude sample (1 g) was loaded onto the column by adsorbing onto 1 g silica gel. The column was eluted with chlorofom stepwise increasing portions of methanol, and finally pure methanol. The flow rate of the eluents was maintained at 2 ml/min. All fractions were collected in 10 ml volume, and concentrated to dryness in a savant concentrator. All fractions were co-chromatographed using thin layer chromatography to aid in pooling different fractions. The flash column chromatography fractions (fraction #15-26; weighing 210 mg) which were colorless, corresponded to a published Myriceric acid. Further isolation and purification of Myriceric acids was carried out via preparative thin layer chromatography.

Preparative thin layer chromatography (tlc): Silica gel thin layer plates (Kieselgel 60 F254, 20×20 cm, 1 mm thickness were used. The pooled (fractions #15-26) fraction (50 mg) was dissolved in ethyl acetate and streaked onto tlc plates (only a portion of the combined fractions 15-26 were subjected to preparative TLC) The plates were then developed with chloroform and methanol (70:30). The plates were visualized by color as well as observing under UV (254 nm) light. The band was scraped off the plate and eluted with ethyl acetate to obtain white granular crystals (12 mg).

Final purification and UV spectral confirmation: Final purification was performed via high pressure liquid chromatography (HPLC). A HP 1090 HPLC with a DR-5 solvent delivery system and diode array detector was used. A 100×2.1 mm column (5 um Hypersil C18 reversed phase) was eluted with water-acetonitrile gradient with a flow rate of 0.6 ml/min. The sample was monitored based on the UV character and the fraction eluting at 12.55 min was collected, dried under nitrogen and finally freeze-dried to obtain white granular pure Myriceric acid A. The UV confirmation to the published Myriceric acid A was made by overlaying the UV spectra (matching~99.00) and also comparing the retention time.

Spectroscopic confirmation: Identification was confirmed by comparing the nuclear magnetic resonance (NMR) spectra, and the mass spectrum (MS) to the published literature [Sakurawi, K. et al. Chem. Pharm. Bull., 44: 353-351 (1996)]. The NMR spectra were measured on a GE500 Omega spectrometer in CDCl3. Low resolution CIMS and EIMS were obtained using a Hewlett-Packard 5985-B mass spectrometer, and HRMS was determined on the A.E.I. MS-902. The compound was found to have a molecular weight of 632 with an elemental composition of $C_{39}H_{52}O_7$. The UV (in methanol) spectrum was also similar to published literature.

PM 2011 (1) inhibits tumor cell lines independent of endothelin receptor A ($ET_A$) inhibition: Others have disclosed PM 2011 (1) and its derivatives as potent endothelin receptor antagonists (WO 92/12991, EP 526,642, U.S. Pat. No. 5,248,807, U.S. Pat. No. 5,463,107 and U.S. Pat. No. 5,587,505). We have used human tumor cell lines to evaluate the effects of PM 2011 (1) on endothelin-1 (ET-1) dependent biologic functions. Some of these cell lines are well characterized for the expression and role of ET-1, $ET_A$ and $ET_B$ (16, 41). Additionally, selective inhibitors of $ET_A$ and $ET_B$, BQ-123 and BQ-788 respectively were used to validate cell lines; inhibition by only one of these inhibitors usually suggests that the biologic effects are mediated through that specific receptor only. To validate three cell lines, we studied the effects of BQ123, BQ788, PM2010, PM2011 and PM2012 on cell proliferation by MTS assay for 72 h (16). Results are shown in Table 1. In agreement with Lahav et al (16), BQ788 inhibited the growth of SK-Mel 28 cell line whereas, no growth inhibition of SK-Mel 28 by BQ123 was observed (Table 1).

HPV-negative cell line C33A neither secretes ET-1 nor expresses $ET_A$ (41); inhibition of C33A by PM 2011 (1) (Table 1) suggests that in addition to $ET_A$ inhibition, activity against additional molecular target(s) may also be contributing towards their antitumor effects.

TABLE 1

| Tumor Cell | $IC_{50}$, $\mu M^a$ or % Inhibition at 100 $\mu M$ (i) | | |
|---|---|---|---|
| Lines | BQ-123 | BQ788 | PM2011 |
| SiHa | 0% i | 45% i | 3.0 |
| SK-Mel-28 | 0% i | 82.0 | 0.9 |
| C33A | 20% i | 61.8 | 1.3 |
| K562 | 30% | 0% i | 1.0 |
| HL60 | 46 | 45 | 2.3 |

To further explore the additional molecular target(s) for PM2011, we postulated that these compounds could antagonize the activation of NF-$_\kappa$B. To test this hypothesis, we evaluated the effects of PM2010, PM2011 and PM2012 on TNF-α-dependent activation of NF-$_\kappa$B binding to $_\kappa$B site in nuclear extracts of HeLa cells by an ELISA (Panomics) as recommended. Results are shown in FIG. 1. A dose-dependent decrease in NF-$_\kappa$B binding to $_\kappa$B site in HeLa cells by PM2011 was observed (FIG. 1).

REFERENCES

1. Makarov S S. "NF-$_\kappa$B as a therapeutic target in chronic inflammation: recent advances." Mol Med Today 6:441-8 (2000).
2. Pahl H L. "Activators and target genes of Rel/NF-$_\kappa$B transcription factors." Oncogene 18:6953-66 (1999).
3. Baldwin A S, Jr. "The NF-$_\kappa$B and I-$_\kappa$B proteins: new discoveries and insights." Annu. Rev. Immunol. 14:649-83 (1996).
4. Ghosh S, May M J, Kopp E B. "NF-$_\kappa$B and Rel proteins: evolutionarily conserved mediators of immune responses." Annu. Rev. Immunol. 16:225-60 (1998).
5. Whiteside S T, Israel A. "I-$_\kappa$B proteins: structure, function and regulation." Semin. Cancer Biol. 8:75-82 (1997).
6. Karin M. Ben-Neriah Y. "Phosphorylation meets ubiquitination: the control of NF-$_\kappa$B activity." Annu. Rev. Immunol. 18:621-663 (2000).
7. Israel A. "The IKK complex: an integrator of all signals that activate NF-.kappa.B." Trends Cell Biol. 10:129-33 (2000).

8. Rothwarf D M, Zandi E, Natoli G, Karin M. "IKK-.gamma. is an essential regulatory subunit of the I-$_\kappa$B kinase complex." Nature 395:297-300 (1998).

9. Yamaoka S, Courtois G, Bessia C, Whiteside S T, Weil R, Agou F, Kirk H E, Kay R J, Israel A. "Complementation cloning of NEMO, a component of the I-$_\kappa$B kinase complex essential for NF-$_\kappa$B activation." Cell 93:1231-40 (1998).

10. Rayet B, Gelinas C. "Aberrant rel/nfkb genes and activity in human cancer." Oncogene 18:6938-47 (1999).

11. Mayo M W, Badwin A S. "The transcription factor NF-.kappa.B: control of oncogenesis and cancer therapy resistance." Biochim. Biophys. Acta 1470:M55-M62 (2000).

12. Romashkova J A, Makarov S S. "NF-$_\kappa$B is a target of AKT in anti-apoptotic PDGF signaling." Nature 401:86-90 (1999).

13. Hinz M, Krappmann D, Eichten A, Heder A, Scheidereit C, Strauss M. "NF-$_\kappa$B function in growth control: regulation of cyclin D1 expression and G.sub.0/G.sub.1-to-S-phase transition." Mol. Cell. Biol. 19:2690-8 (1999).

14. Barkett M, Gilmore T D. "Control of apoptosis by Rel/NF-$_\kappa$B transcription factors." Oncogene 18:6910-24 (1999).

15. Gasparian A V, Yao Y J, Lu J, Yemelyanov A Y, Lyakh L A, Slaga T J, Budunova I V. "Selenium compounds inhibit I-$_\kappa$B kinase (IKK) and nuclear factor-.kappa.B (NF-.kappa.B) in prostate cancer cells." Mol Cancer Ther. 1:1079-87 (2002).

16. Yamamoto Y, Gaynor R B. "Therapeutic potential of inhibition of the NF-$_\kappa$B pathway in the treatment of inflammation and cancer." J. Clin. Invest. 107135-42 (2001).

17. Shen W, Waldschmidt M, Zhao X, Ratliff T, Krieg A M. "Antitumor mechanisms of oligodeoxynucleotides with CpG and polyG motifs in murine prostate cancer cells: decrease of NF-$_\kappa$B and AP-1 binding activities and induction of apoptosis." Antisense Nucleic Acid Drug Dev. 12:155-64 (2002).

18. Karin M. "New twists in gene regulation by glucocorticoid receptor: is DNA binding dispensable?" Cell 93:487-90 (1998).

19. Yang J P, Merin J P, Nakano T, Kato T, Kitade Y, Okamoto T. "Inhibition of the DNA-binding activity of NF-$_\kappa$B by gold compounds in vitro." FEBS Lett. 361:89-96 (1995).

20. Yin M J, Yamamoto Y, Gaynor R B. "The anti-inflammatory agents aspirin and salicylate inhibit the activity of I-$_\kappa$B kinase-.beta." Nature 396:77-80 (1998).

21. Epinat J C, Gilmore T D. "Diverse agents act at multiple levels to inhibit the RelI/NF-$_\kappa$B signal transduction pathway." Oncogene 18:6896-6909 (1999).

22. Jobin C, Bradham C A, Russo M P, Juma B, Narula A S, Brenner D A, Sartor R B. "Curcumin blocks cytokine-mediated NF-$_\kappa$B activation and proinflammatory gene expression by inhibiting inhibitory factor I-.kappa.B kinase activity." J. Immunol. 163:3474-83 (1999).

23. Tomita T, Takeuchi E, Tomita N, Morishita R, Kaneko M, Yamamoto K, Nakase T, Seki H, Kato K, Kaneda Y, Ochi T. "Suppressed severity of collagen-induced arthritis by in vivo transfection of nuclear factor kappa B decoy oligodeoxynucleotides as a gene therapy." Arthritis Rheum. 42:2532-42 (1999).

24. Bantel H, Schmitz M L, Raible A, Gregor M, Schulze-Osthoff K. "Critical role of NF-$_\kappa$B and stress-activated protein kinases in steroid unresponsiveness." FASEB J. 16:1832-34 (2002).

25. Kaltschmidt B, Uherek M, Wellmann H, Volk B, Katschmidt C. "Inhibition of NF-$_\kappa$B potentiates amyloid beta-mediated neuronal apoptosis." Proc. Natl. Acad. Sci., U.S.A. 96:9409-14 (1999).

26. Bates P J, Kahlon J B, Thomas S D, Trent J O, Miller D M "Antiproliferative activity of G-rich oligonucleotides correlates with protein binding." J. Biol. Chem. 274:26369-77 (1999).

27. Derenzini M, Sirri V, Trere D, Ochs R L. "The quantity of nucleolar proteins nucleolin and protein B23 is related to cell doubling time in human cancer cells." Lab. Invest. 73:497-502 (1995).

28. Roussel P, Sirri V, Hernandez-Verdun D. "Quantification of Ag—NOR proteins using Ag—NOR staining on western blots." J. Histochem Cytochem. 42:1513-7 (1994).

29. Pich A, Chiusa L, Margaria E. "Prognostic relevance of AgNORs in tumor pathology." Micron. 31:133-41 (2000).

30. Trere D, Derenzini M, Sirri V, Montanaro L, Grigioni W, Faa G, Columbano G M, Columbano A. "Qualitative and quantitative analysis of AgNOR proteins in chemically induced rat liver carcinogenesis." Hepatology 24:1269-73 (1996).

31. Data derived from genome.ucsc.edu (to locate nucleolin sequence at 2q37.1) and the Mitelman Database of Chromosome Aberrations in Cancer (cgap.nci.nih.gov/Chromosomes).

32. Srivastava M, Pollard H B. "Molecular dissection of nucleolin's role in growth and cell proliferation: new insights." FASEB J. 13:1911-22 (1999).

33. Tuteja R, Tuteja N. "Nucleolin: a multifunctional major nucleolar phosphoprotein." Crit. Rev. Biochem. Mol. Biol. 33:407-36 (1998).

34. Ginisty H, Sicard H, Roger B, Bouvet P. "Structure and functions of nucleolin." J. Cell. Sci. 112 (Pt 6):761-72 (1999).

35. Yang C, Maiguel D A, Carrier F. "Identification of nucleolin and nucleophosmin as genotoxic stressresponsive RNA-binding proteins." Nucleic Acids Res. 30:2251-60 (2002).

36. Daniely Y, Borowiec J A. "Formation of a complex between nucleolin and replication protein A after cell stress prevents initiation of DNA replication." J. Cell Biol. 149:799-810 (2000).

37. Wang Y, Guan J, Wang H, Wang Y, Leeper D, lliakis G. "Regulation of dna replication after heat shock by replication protein a-nucleolin interactions." J. Biol. Chem. 276:20579-88 (2001).

38. Bates P J, Miller D M, Trent J O, Xu, X. "Method for the diagnosis and prognosis of malignant diseases," U.S. patent application Ser. No. 10/118,854, filed in the USPTO on Apr. 8, 2002.

39. Barel M, Le Romancer M, Frade R. "Activation of the EBV/C3d receptor (CR2, CD21) on human B lymphocyte surface triggers tyrosine phosphorylation of the 95-kDa nucleolin and its interaction with phosphatidylinositol 3 kinase." J. Immunol. 166:3167-73 (2001).

40. Larrucea S, Cambronero R, Gonzalez-Rubio C, Fraile B, Gamallo C, Fontan G, Lopez-Trascasa M. "Internalization of factor J and cellular signalization after factor J-cell interaction." Biochem. Biophys. Res. Commun. 266:51-7 (1999).

41. Dumler I, Stepanova V, Jerke U, Mayboroda O A, Vogel F, Bouvet P, Tkachuk V, Haller H, Gulba D C. "Urokinase-induced mitogenesis is mediated by casein kinase 2 and nucleolin." Curr. Biol. 9:1468-76 (1999).

42. Hovanessian A G, Puvion-Dutilleul F, Nisole S, Svab J, Perret E, Deng J S, Krust B. "The cell-surface expressed nucleolin is associated with the actin cytoskeleton." Exp. Cell Res. 261:312-28 (2000).

43. Callebaut C, Blanco J, Benkirane N, Krust B, Jacotot E, Guichard G, Seddiki N, Svab J, Dam E, Muller S, Briand J P, Hovanessian A G. "Identification of V3 loop-binding proteins as potential receptors implicated in the binding of HIV particles to CD4(+) cells." J. Biol. Chem. 273:21988-97 (1998).

44. Borer R A, Lehner C F, Eppenberger H M, Nigg E A. "Major nucleolar proteins shuttle between nucleus and cytoplasm." Cell 56:379-90 (1989).

45. Martin P, Duran A, Minguet S, Gaspar M L, Diaz-Meco M T, Rennert P, Leitges M, Moscat J. "Role of zeta PKC in B-cell signaling and function." EMBO J. 21:4049-57 (2002).

46. Zhou G, Seibenhener M L, Wooten M W. Nucleolin is a protein kinase C-zeta substrate. Connection between cell surface signaling and nucleus in PC12 cells." J. Biol. Chem. 272:31130-7 (1997).

47. Turutin D V, Kubareva E A, Pushkareva M A, Ullrich V, Sud'ina G F. "Activation of NF-kappa B transcription factor in human neutrophils by sulphatides and L-selectin cross-linking." FEBS Lett. 536:241-5 (2003).

48. Harms G, Kraft R, Grelle G, Volz B, Dernedde J, Tauber R. "Identification of nucleolin as a new L selectin ligand." Biochem. J. 360(Pt 3):531-8 (2001).

49. Salazar R, Brandt R, Krantz S. "Binding of Amadori glucose-modified albumin by the monocytic cell line Mono-Mac 6 activates protein kinase C.epsilon. protein tyrosine kinases and the transcription factors AP-1 and NF-.kappa.B." Glycoconj J. 18:769-77 (2001).

50. Sugano N, Chen W, Roberts M L, Cooper N R. "Epstein-Barr virus binding to CD21 activates the initial viral promoter via NF-$_κ$B induction." J. Exp Med. 186:731-7 (1997).

51. Gil D, Gutierrez D, Alarcon B. "Intracellular redistribution of nucleolin upon interaction with the CD3.epsilon.chain of the T cell receptor complex." J. Biol. Chem. 276: 11174-9 (2001).

52. Weil R, Schwamborn K, Alcover A, Bessia C, Di Bartolo V, Israel A. "Induction of the NF-$_κ$B cascade by recruitment of the scaffold molecule NEMO to the T cell receptor." Immunity 18:13-26 (2003).

53. Miranda G A, Chokler I, Aguilera R J. "The murine nucleolin protein is an inducible DNA and ATP binding protein which is readily detected in nuclear extracts of lipopolysaccharide-treated splenocytes." Exp. Cell Res. 217: 294-308 (1995).

54. Hauser H, Gains N. Spontaneous vesiculation of phospholipids: a simple and quick method of forming unilamellar vesicles. Proc. Natl. Acad. Sci., U.S.A. 79:1683-7 (1982).

55. Pitcher W H III, Huestis W H. "Preparation and analysis of small unilamellar phospholipid vesicles of a uniform size." Biochem. Biophys. Res. Commun. 296:1352-5 (2002).

56. Wang H, Yu D, Agrawal S, Zhang R. "Experimental therapy of human prostate cancer by inhibiting MDM2 expression with novel mixed-backbone antisense oligonucleotides: In vitro and in vivo activities and mechanisms." Prostate 54:194-205 (2003).

57. Chi K N, Gleave M E, Klasa R, Murray N, Bryce C, Lopes de Menezes D E, D'Aloisio S, Tolcher A W. "A phase I dose-finding study of combined treatment with an antisense Bcl-2 oligonucleotide (Genasense) and mitoxantrone in patients with metastatic hormone-refractory prostate cancer." Clin. Cancer Res. 7, 3920-3927 (2001).

58. Coqueret O, Gascan H. "Functional interaction of STAT3 transcription factor with the cell cycle inhibitor p21WAF1/CIP1/SDI1." J. Biol. Chem. 275:18794-800 (2000).

59. Jensen O, Wilm M, Shevchenko A, Mann M. "Peptide sequencing of 2-DE gel-isolated proteins by nanoelectrospray tandem mass spectrometry." Methods Mol. Biol. 112: 513-30 (1999).

60. Kikuchi E, Horiguchi Y, Nakashima J, Kuroda K, Oya M, Ohigashi T, Takahashi N, Shima Y, Umezawa K, Murai M. "Suppression of hormone-refractory prostate cancer by a novel nuclear factor KB inhibitor in nude mice." Cancer Res. 63:107-10 (2003).

61. Nabel, E G, Nabel, G J. "Treatment of diseases by site-specific instillation of cells or site-specific transformation of cells and kits therefore." U.S. Pat. No. 5,328,470. (1994).

62. Chen, S. H., H. D. Shine, J. C. Goodman, R. G. Grossman, et al. 1994. Gene therapy for brain tumors: regression of experimental gliomas by adenovirus-mediated gene transfer in vivo. Proc Natl Acad Sci USA. 91:3054-7.

What is claimed is:

1. A method of treating inflammatory bowel disease in a mammal in need of such treatment comprising administering an effective amount of a NF-$_κ$B inhibitory composition of the formula:

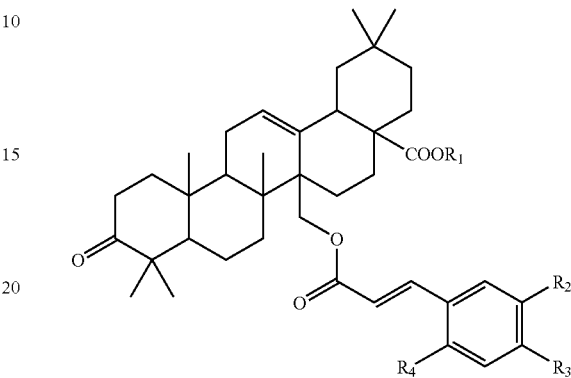

wherein $R_1$ is hydrogen or a metabolic ester residue; $R_2$ and $R_3$ each independently or together are hydrogen or hydroxy; $R_4$ is hydrogen or $NHR_5$; wherein $R_5$ is $R_6$-$R_7$; wherein $R_6$ is —SO3-, —COCOO—, or —COR$_8$COO— ($R_8$ is an alkyl chain of 1 to 6 carbon atoms or an bearing chain of 2 to 6 carbon atoms) and $R_7$ is hydrogen or a metabolic ester residue or a pharmaceutically acceptable salt thereof.

2. A method according to claim 1 wherein the compound is myriceric acid A.

3. A method of treating inflammatory bowel disease characterized by pathological NF-$_κ$B activation comprising inhibiting the pathological activation by administering to a patient in need thereof an effective amount of a compound:

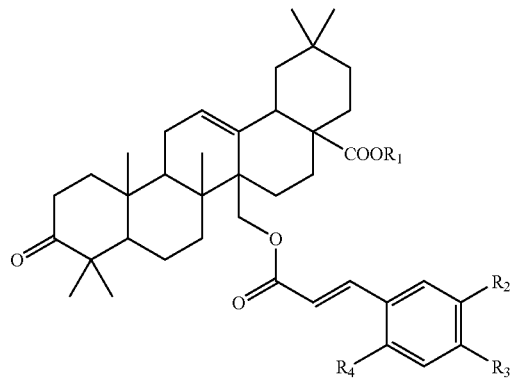

wherein $R_1$ is hydrogen or a metabolic ester residue; $R_2$ and $R_3$ each independently or together are hydrogen or hydroxy; $R_4$ is hydrogen or $NHR_5$; wherein $R_5$ is $R_6$-$R_7$; wherein $R_6$ is —SO3-, —COCOO—, or —COR$_8$COO— ($R_8$ is an alkyl chain of 1 to 6 carbon atoms or an alkene-bearing chain of 2 to 6 carbon atoms) and $R_7$ is hydrogen or a metabolic ester residue or a pharmaceutically acceptable salt thereof.

* * * * *